United States Patent

Hatfield et al.

[11] Patent Number: 6,126,603
[45] Date of Patent: Oct. 3, 2000

[54] METHOD AND APPARATUS FOR SEGMENTING COLOR FLOW MODE DATA USING VELOCITY INFORMATION IN THREE-DIMENSIONAL ULTRASOUND IMAGING

[75] Inventors: William Thomas Hatfield, Schenectady, N.Y.; Todd Michael Tillman, West Milwaukee; Patricia A. Schubert, Milwaukee, both of Wis.

[73] Assignee: General Electric Company, Milwaukee, Wis.

[21] Appl. No.: 08/852,613

[22] Filed: May 7, 1997

[51] Int. Cl.[7] ........................................... A61B 8/00
[52] U.S. Cl. ............................. 600/454; 600/443
[58] Field of Search ........................... 128/916; 600/443, 600/454, 447, 449

[56] References Cited

U.S. PATENT DOCUMENTS

| | | | |
|---|---|---|---|
| 5,226,113 | 7/1993 | Cline et al. | 395/124 |
| 5,329,929 | 7/1994 | Sato et al. | 128/916 |
| 5,353,220 | 10/1994 | Ito et al. | 128/916 |
| 5,365,929 | 11/1994 | Peterson | 128/661.1 |
| 5,474,073 | 12/1995 | Schwartz et al. | 128/661.1 |
| 5,485,842 | 1/1996 | Quistgaard | 128/660.07 |
| 5,582,173 | 12/1996 | Li | 128/660.07 |
| 5,622,174 | 4/1997 | Yamazaki | 600/443 |
| 5,655,535 | 8/1997 | Friemel et al. | 128/600.07 |

FOREIGN PATENT DOCUMENTS

WO 97/00482   1/1997   WIPO.

*Primary Examiner*—Marvin M. Lateef
*Assistant Examiner*—Maulin Patel
*Attorney, Agent, or Firm*—Ostrager Chong & Flaherty; Christian G. Cabou; Phyllis Y. Price

[57] ABSTRACT

A method and an apparatus for segmenting three-dimensional projected velocity images by limiting the volume of velocity data projected onto the imaging planes. If the volume of interest contains flowing blood, i.e., an artery or vein, the Doppler shift present in the ultrasound reflected from the flowing blood can be detected and then used to limit the amount of velocity data which is projected. Only pixels having velocity values within a predetermined range are projected onto the imaging plane.

11 Claims, 6 Drawing Sheets

METHOD AND APPARATUS FOR SEGMENTING COLOR FLOW MODE DATA USING VELOCITY INFORMATION IN THREE-DIMENSIONAL ULTRASOUND IMAGING

FIELD OF THE INVENTION

This invention generally relates to ultrasound imaging of the human anatomy for the purpose of medical diagnosis. In particular, the invention relates to a method and an apparatus for three-dimensional imaging of moving fluid or tissue in the human body by detecting Doppler shifting of ultrasonic echoes reflected from the moving fluid or tissue.

BACKGROUND OF THE INVENTION

Conventional ultrasound scanners create two-dimensional B-mode images of tissue in which the brightness of a pixel is based on the intensity of the echo return. In color flow imaging, the flow of blood or movement of tissue can be imaged. Measurement of blood flow in the heart and vessels using the Doppler effect is well known. The frequency shift of backscattered ultrasound waves may be used to measure the velocity of the back-scatterers from tissue or blood. The change or shift in backscattered frequency increases when blood flows toward the transducer and decreases when blood flows away from the transducer. The Doppler shift may be displayed using different colors to represent speed and direction of flow. The color flow mode displays hundreds of adjacent sample volumes simultaneously, all color-coded to represent each sample volume's velocity. The color flow image may be superimposed on the B-mode image.

The present invention is incorporated in an ultra-sound imaging system consisting of four main subsystems: a beamformer 2 (see FIG. 1), processor subsystem 4, a scan converter/display controller 6 and a master controller 8. System control is centered in master controller 8, which accepts operator inputs through an operator interface (not shown) and in turn controls the various subsystems. The master controller also generates the system timing and control signals which are distributed via a system control bus 10 and a scan control bus (not shown).

Figure 1:
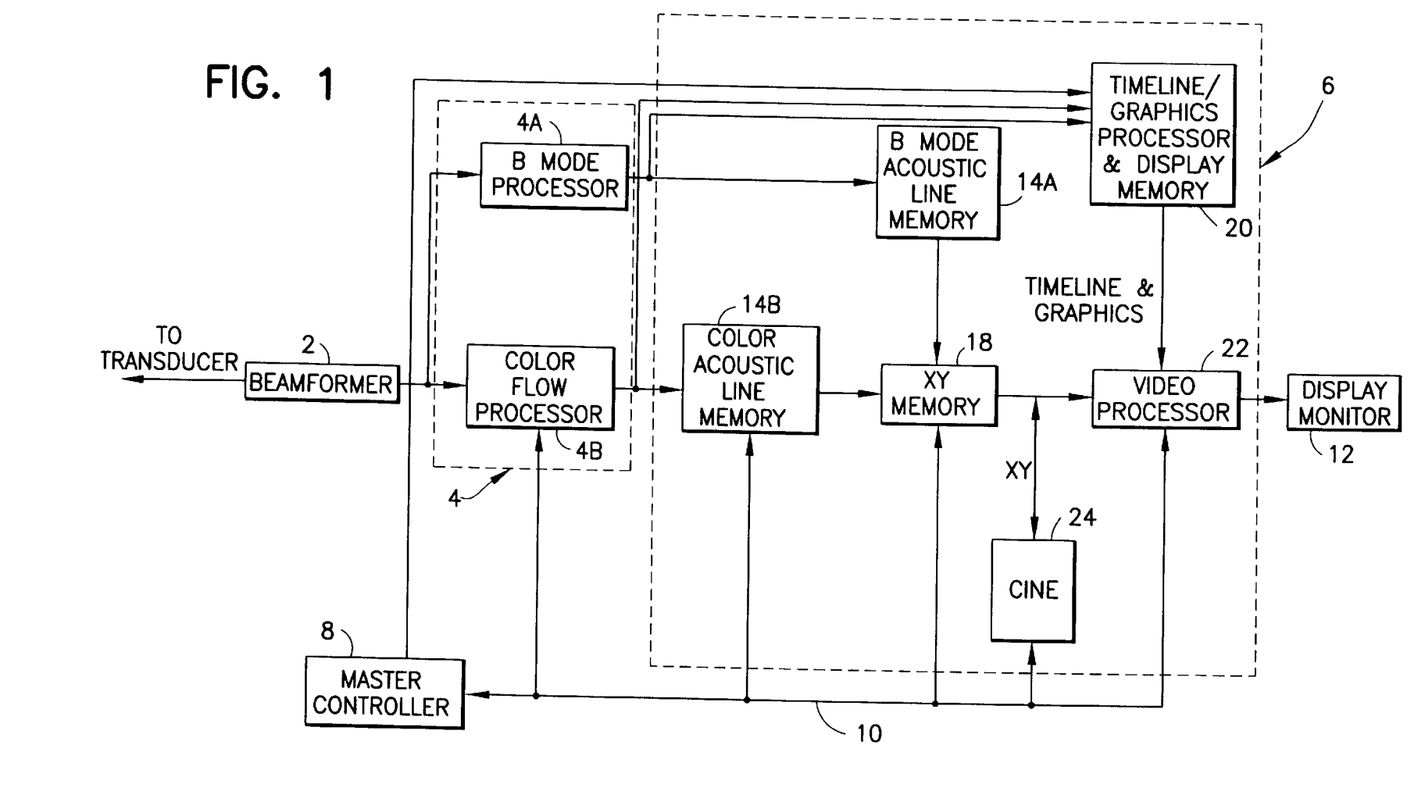
FIG. 1 is a block diagram showing the major functional subsystems within a real-time ultrasound imaging system.

The main data path begins with the digitized RF inputs to the beamformer from the transducer. The beam-former outputs two summed digital baseband receive beams. The baseband data is input to B-mode processor 4A and color flow processor 4B, where it is processed according to the acquisition mode and output as processed acoustic vector (beam) data to the scan converter/display processor 6. The scan converter/display processor 6 accepts the processed acoustic data and outputs the video display signals for the image in a raster scan format to a color monitor 12. The scan converter/display controller 6, in cooperation with master controller 8, also formats multiple images for display, display annotation, graphics overlays and replay of cine loops and recorded timeline data.

The B-mode processor 4A converts the baseband data from the beamformer into a log-compressed version of the signal envelope. The B function images the time-varying amplitude of the envelope of the signal as a grey scale using an 8-bit output for each pixel. The envelope of a baseband signal is the magnitude of the vector which the baseband data represent.

The frequency of sound waves reflecting from the inside of blood vessels, heart cavities, etc. is shifted in proportion to the velocity of the blood cells: positively shifted for cells moving towards the transducer and negatively for those moving away. The color flow (CF) processor 4B is used to provide a real-time two-dimensional image of blood velocity in the imaging plane. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. The structure and operation of a color flow processor are disclosed in U.S. Pat. No. 5,524,629, the contents of which are incorporated by reference herein.

The color flow processor produces velocity (8 bits), variance (turbulence) (4 bits) and power (8 bits) signals. The operator selects whether the velocity and variance or the power are output to the scan converter. The output signal is input to a chrominance control lookup table which resides in the video processor 22. Each address in the lookup table stores 24 bits. For each pixel in the image to be produced, 8 bits control the intensity of red, 8 bits control the intensity of green and 8 bits control the intensity of blue. These bit patterns are preselected such that as the flow velocity changes in direction or magnitude, the color of the pixel at each location is changed. For example, flow toward the transducer is indicated as red and flow away from the transducer is indicated as blue. The faster the flow, the brighter the color.

The acoustic line memories 14A and 14B of the scan converter/display controller 6 respectively accept processed digital data from processors 4A and 4B and perform the coordinate transformation of the color flow and B-mode data from polar coordinate (R-θ) sector format or Cartesian coordinate linear array to appropriately scaled Cartesian coordinate display pixel data stored in X-Y display memory 18. In the B-mode, intensity data is stored X-Y display memory 18, each address storing three 8-bit pixels. Alternatively, in the color flow mode, data is stored in memory as follows: intensity data (8 bits), velocity or power data (8 bits) and variance (turbulence) data (4 bits).

A multiplicity of successive frames of color flow or B-mode data are stored in a cine memory 24 on a first-in, first out basis. The cine memory is like a circular image buffer that runs in the background, continually capturing image data that is displayed in real time to the user. When the user freezes the system, the user has the capability to view image data previously captured in cine memory. The graphics data for producing graphics overlays on the displayed image is generated and stored in the timeline/graphics processor and display memory 20. The video processor 22 multiplexes between the graphics data, image data, and timeline data to generate the final video output in a raster scan format on video monitor 12. Additionally it provides for various greyscale and color maps as well as combining the greyscale and color images.

A conventional ultrasound imaging system collects B-mode or color flow mode images in cine memory 24 on a continuous basis. The cine memory 24 provides resident digital image storage for single image review and multiple image loop review and various control functions. The region of interest displayed during single-image cine replay is that used during the image's acquisition. The cine memory also acts as a buffer for transfer of images to digital archival devices via the master controller 8.

Two-dimensional ultrasound images are often hard to interpret due to the inability of the observer to visualize the two-dimensional representation of the anatomy being scanned. However, if the ultrasound probe is swept over an area of interest and two-dimensional images are accumulated to form a three-dimensional volume, the anatomy becomes much easier to visualize for both the trained and untrained observer. In particular, three-dimensional ultrasound imaging of moving fluid or tissue would be advantageous.

SUMMARY OF THE INVENTION

The present invention is a method and an apparatus for displaying a three-dimensional image of moving fluid or tissue using velocity Doppler shift data. Segmentation of the image is improved by limiting the volume of pixel data projected onto the imaging planes. In accordance with the present invention, if the volume of interest contains moving fluid or tissue, the Doppler shift present in the ultrasound reflected from the moving fluid or tissue can be detected and then used to limit the amount of pixel data to be projected.

The apparatus incorporating the invention comprises an ultrasound scanner which collects color flow mode images in a cine memory in response to a periodic external trigger event, such as the occurrence of a pre-determined characteristic, e.g., a peak, in a patient's cardiac cycle. In accordance with the invention, each acquired pixel comprises an 8-bit velocity value derived from any Doppler shift detected in the echo return signal reflected from each respective sample volume. The velocity information is processed to identify the velocity data to be projected by a master controller (or a separate dedicated processor) onto the imaging planes. The velocity data is processed by retrieving each velocity datum having a magnitude which falls within a pre-determined range, e.g., velocity data which has a non-zero magnitude. In accordance with the broad concept of the invention, velocity values greater than a minimum threshold or less than a maximum threshold or lying between minimum and maximum thresholds may be retrieved from the cine memory for projection. Pixels in this category are used to define a source pixel data volume for use in reconstructing projected images. The pixels included in the source pixel data volume are used in reconstructing projections onto various imaging planes. Pixels outside the source data volume are not used in the reconstruction. The result is projected velocity images that have excellent segmentation.

To image moving fluid or tissue in three dimensions, the master controller performs an algorithm that projects the pixel velocity data in the source data volume onto a plurality of rotated image planes using a ray-casting technique. The projected data resulting from each projection is then returned to the cine memory. The projected data is stored for display in a central region of the display image. The perimeter of the display image may optionally include unprojected velocity data taken from the last frame read from the X-Y memory prior to freezing of the system by the operator. Alternatively, the projected velocity image can be displayed without unprojected data from any back-ground frame.

In accordance with the method of the invention, the master controller retrieves velocity data from the cine memory. That velocity data is stored in the cine memory in response to the occurrence of a predetermined characteristic, e.g., a peak, in a patient's cardiac cycle waveform. In one acquisition mode, one frame per cycle is transferred from the X-Y memory to the cine memory. The velocity data from the volume of interest is then processed in accordance with the aforementioned thresholding scheme to acquire the velocity source data volume to be projected onto various imaging planes. In a different acquisition mode, multiple successive frames are stored in cine memory at the acoustic frame rate in response to the trigger event. Then the velocity data is processed as previously described to reconstruct projected images, which are returned to cine memory. The reconstructed frames stored in cine memory can then be displayed selectively by the system operator.

DETAILED DESCRIPTION OF THE PREFERRED EMBODIMENTS

Figure 2:
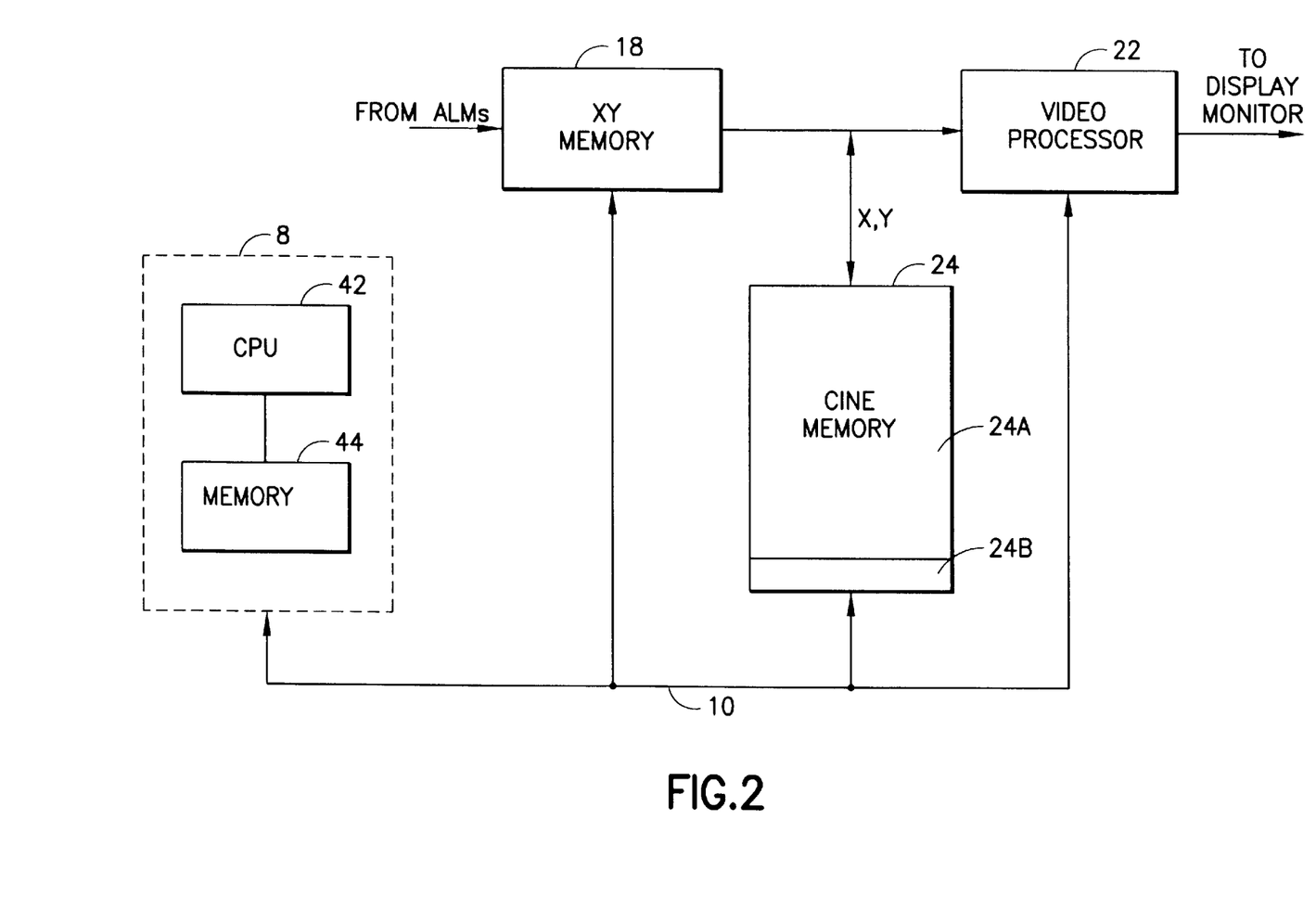
FIG. 2 is a block diagram showing the means for reconstructing frames comprising successive volumetric projections of pixel intensity data in accordance with the invention.

Referring to FIG. 2, the master controller 8 comprises a central processing unit (CPU) 42 and a random access memory 44. The CPU 42 has read only memory incorporated therein for storing routines used in transforming an acquired volume of velocity and turbulence data into a multiplicity of three-dimensional projection images taken at different angles. The CPU 42 controls the X-Y memory 18 and the cine memory 24 via the system control bus 10. In particular, the CPU 42 controls the flow of data from the X-Y memory 18 to the video processor 22 and to the cine memory 24, and from the cine memory to the video processor 22 and to the CPU 42 itself. When the ultrasound imaging system is operating in the color flow mode, each frame of color flow data, representing one of a multiplicity of scans or slices through the object being examined, is stored in the X-Y memory 18 and in the next cycle is transmitted to video processor 22 and to cine memory 24. A stack of frames, representing the scanned object volume, is stored in section 24A of cine memory 24. During initialization (see step 26 in FIG. 3), the CPU 42 retrieves from cine memory section 24A only the color flow data corresponding to an object volume of interest. This is accomplished by retrieving only the color flow data in a region of interest from each selected frame. The color flow data corresponding to the region of interest from each one of a multiplicity of selected frames forms a source data volume of interest.

In accordance with the preferred embodiment of the invention, the source data volume of interest comprises those pixels having a velocity component within a predetermined range, e.g., having non-zero velocity values. The velocity data in the source data volume is then used to reconstruct projected images taken at different viewing angles.

The velocity projections are reconstructed in CPU 42, which performs a series of transformations using the ray-casting algorithm disclosed in U.S. Pat. No. 5,226,113. The successive transformations represent maximum, minimum or averaged velocity projections made at angular increments, e.g., at 10° intervals, within a range of angles, e.g., +90° to −90°. However, the angular increment need not be 10°; nor is the invention limited to any particular range of angles.

In accordance with the ray casting technique employed in the present invention, volumetrically rendered projection images of a sample 50 (see FIG. 4) is displayed from any arbitrary viewing angle, e.g. a spherical projection angle denoted by angle parameters (θ,φ), where θ is the angle that an extension 58' of a viewing ray 58 makes upon the X-Y plane, and φ is the angle of ray 58 with respect to extension 58', by scanning an object volume 52 an ultrasound transducer. Sample volume 52 is scanned in such a manner as to create a series of stacked, contiguous slices or sheets $OS_1$, $OS_2, \ldots, OS_k$, each of which contains the same number of object volume elements (voxels) OV. Each voxel has a rectangular profile in the sheet plane (say, the X-Y plane); while the complementary sides may be of equal length S, so that this profile may be square, the sheet thickness T is generally not equal to the length of either side. Thus, the first object slice $OS_1$ contains a first multiplicity of object voxels $OV_{ij,1}$, where i and j are the respective X-axis and Y-axis positions of the voxel. Similarly, the second object slice $OS_2$ contains object voxels $OV_{ij,2}$. An arbitrary object slice $OS_k$ contains voxels $OV_{ij,k}$, where k is the Z-axis position of that voxel.

Figure 4:
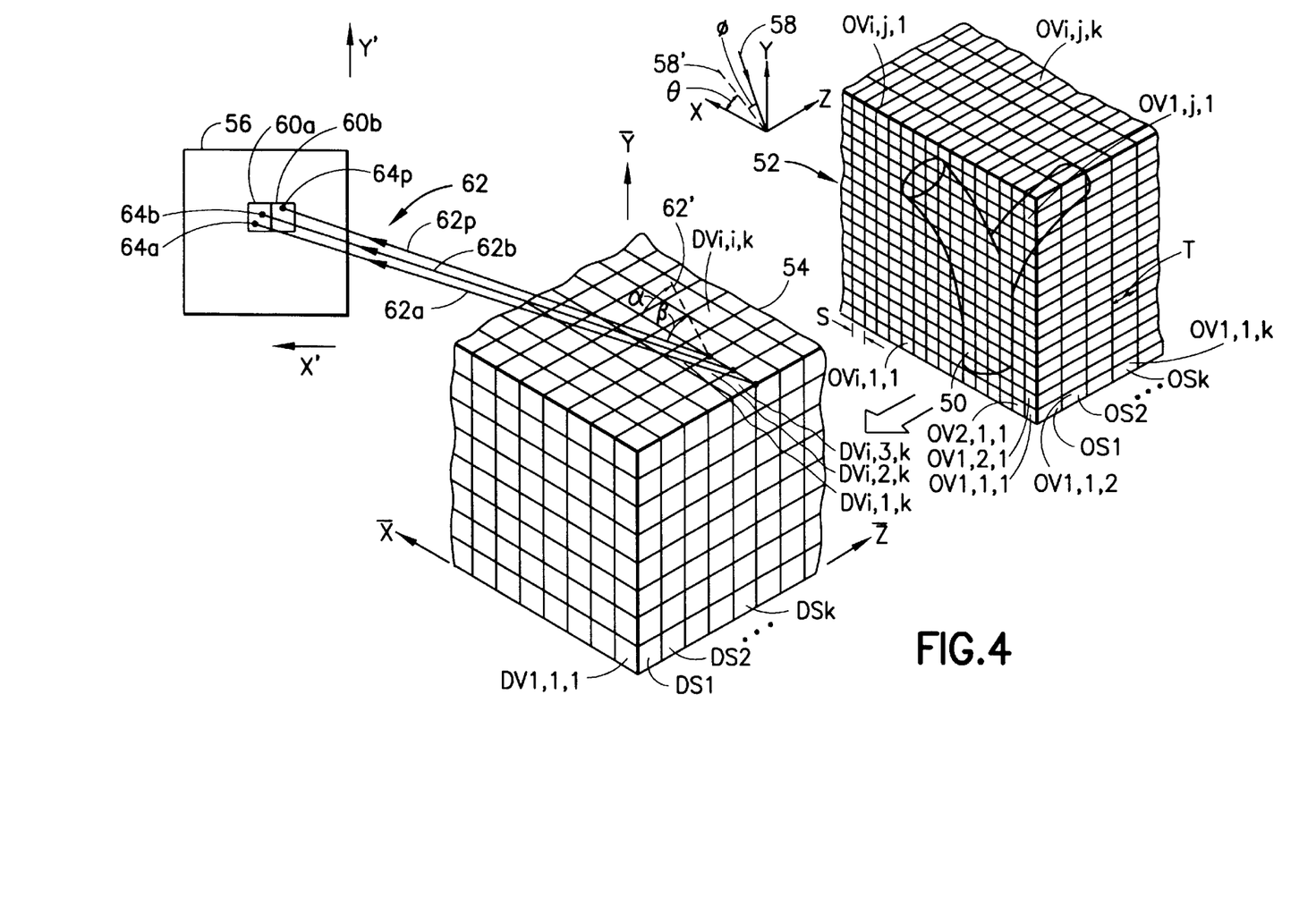
FIG. 4 is a schematic of the sampled object volume of interest, an associated data volume and an image projection plane involved in volumetrically rendering a reversed ray-cast projection in accordance with the prior art.

Each object voxel $OV_{ij,k}$ is analyzed and the data value (intensity, velocity or power) thereof is placed in a corresponding data voxel $DV_{ij,k}$ of a data volume 54. Data volume 54 is a simple cubic i,j,k lattice, even though the thickness of each object slice $OS_k$ and each object voxel face size (the size of the voxel in the X-Y plane) will generally not be the same. That is, not only may the object volume have different X, Y and Z dimensions for each voxel, but also the total number of voxels in any dimension need not be the same. For example, a typical ultrasound three-dimensional scan may provide each slice with a 256×256 matrix of voxels, and may involve 128 slices.

In accordance with a known technique employed by CPU 42, an image of object 50 is projected (step 34 in FIG. 3) by ray casting toward the image plane 56 from a lattice point in data voxel $DV_{ij,k}$. For convenience, the lattice point may, for example, be the data voxel vertex closest to the data volume origin. The cast ray 62 leaves the data volume 54 at a projection angle with spherical angular parameters (α,β) transformed from the spherical angular parameters (θ,φ) at which the object volume 52 is viewed. These two angles are not the same, due to the geometric distortion caused by use of a cubic data volume 54 with a non-cubic object volume 52. However, the projected ray 62 has an X̄-Ȳ plane extension 62' which makes an angle α with respect to the X̄ axis of the data volume, and ray 62 makes an angle β with the Z axis. Thus, angles α and β are determined by a rotation process (to be discussed hereinbelow) to correspond to viewing the object volume 52 at the desired viewing angle (θ,φ) (assuming operation in spherical coordinates). Each of the rays 62 is cast from the data volume voxel lattice point toward the image plane.

While all rays 62 impinge upon some portion of the image plane, only those rays falling within the image plane pixel 60a under consideration are allowed to contribute to the data for that image plane pixel. Thus, having chosen a portion of the object volume 52 to view and a viewing angle (θ,φ) at which to view this selected object volume, the data value in each voxel of the corresponding portion of the data volume is cast at some angle (α,β) (corresponding to viewing the distorted data volume with respect to the object volume) toward the image plane 56. The data value in a first voxel (say, voxel $DV_{i,1,k}$) is thus back-projected along ray 62a, in accordance with the θ and φ values chosen. This ray 62a impinges upon image plane 56 at a position 64a within pixel 60a, and, as this is the first ray to impinge upon this pixel, the intensity, velocity or power value of the incident data is attributed to (stored in) the desired pixel 60a. The next voxel in the data volume (say voxel $DV_{i,2,k}$) has its associated ray 62b projected at the same angular (α,β) configuration from the voxel lattice point, and its position 64b upon image plane 56 is noted. Assuming that impingement position 64b is within desired pixel 60a, the second projected value is (for a maximum pixel projection) compared with the now stored first value and the larger value is placed in storage for pixel 60a. It will be understood that, for an averaged-value projection, the value of a current projected data voxel is added to the sum already stored for the image panel pixel upon which that projection ray impinges, and the sum is eventually divided by a counted number of such impinging rays for that pixel. As each voxel in the selected data volume is sequentially entered and projected toward image plane 56, a data volume voxel (say, voxel $DV_{i,3,k}$) is eventually projected along its associated ray 62p and does not impinge within the desired pixel 60a, so that its data value (e.g., intensity) is not compared to the data value presently stored for pixel 60a. The maximum data value for pixel 60a is now established, for that projection of the data at the particular (θ,φ) three-dimensional angle of view. However, the ray 62p does, in fact, have an impingement point 64p which falls within another image plane pixel (say, pixel 60b) and is compared to the data value stored therein and the larger value is, after the comparison, returned to storage for that pixel. All data values are reset to zero when a new projection is to be taken. Thus, each of the image plane pixels is reset at the start of an image projection procedure, and all of the data volume voxels (in the entire space or in the selected portion, as set by the portion of the object volume 52 selected) are individually and sequentially scanned. The data value in each data voxel DV is projected through an associated ray 62 to impinge upon image plane 56 in one pixel 60 thereof, with the maximum value in each pixel being compared between the present value of the ray-casted data volume voxel, to determine the larger thereof, which larger value is then stored as part of the maximum value image. In practice, for a maximum pixel projection, the stored maximum value will be changed only if the newly cast data voxel value is greater than the data value already stored for the image plane pixel upon which the newly cast ray impinges.

Figure 5:
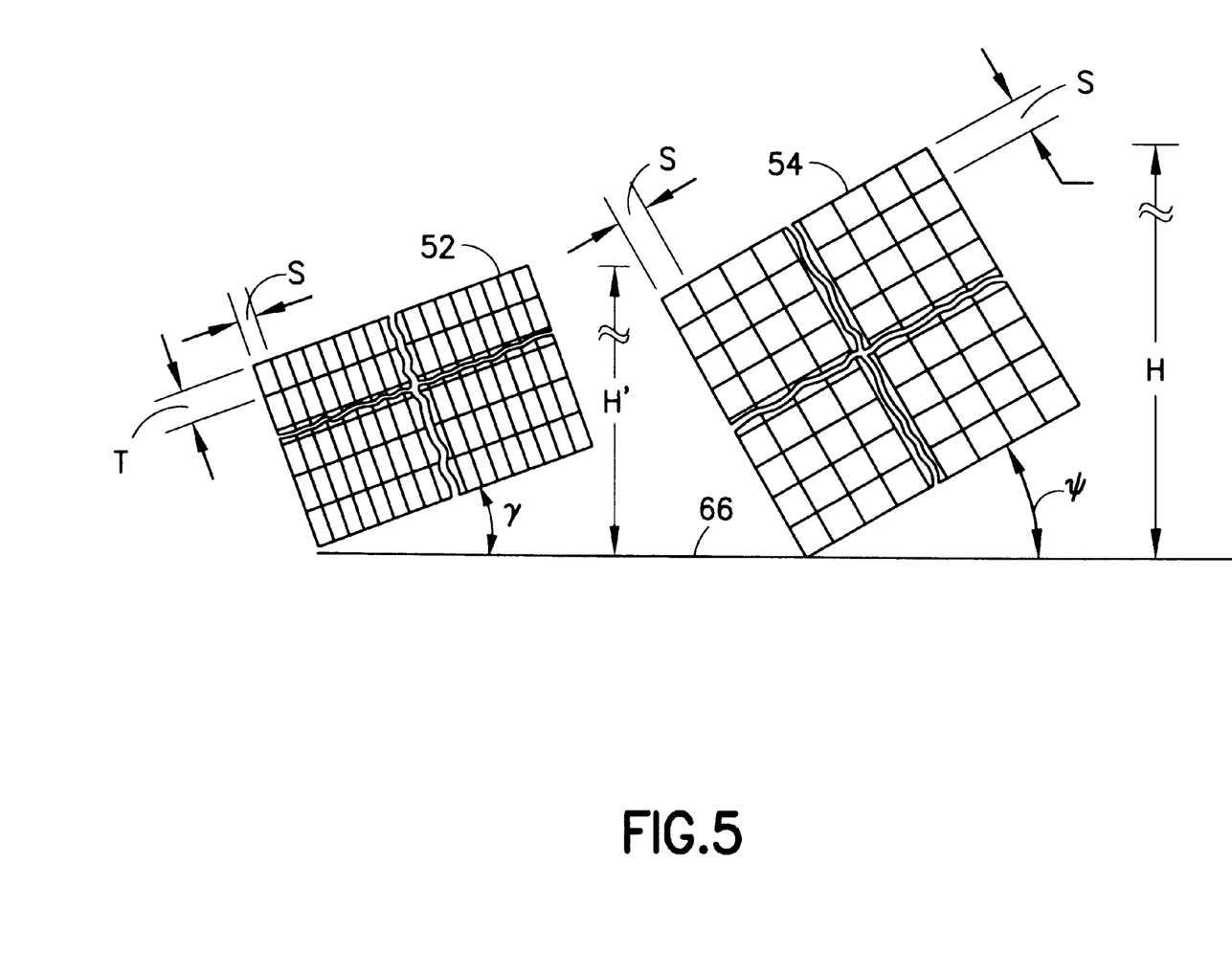
FIG. 5 is a schematic showing a pair of geometric two-dimensional configurations corresponding to like views of object and data volumes, and useful in defining necessary scaling constants in three-dimensional ultrasound imaging.

In accordance with another aspect of the foregoing technique, the data projection is scaled (step 36 in FIG. 3) and any anisotropy between the object volume and the image plane is removed by only a single set of calculations after back projection is complete. Referring now to FIG. 5, because object volume 52 is a real volume while data volume 54 is an abstract concept, it is necessary to determine the amount of distortion of the data projection due to the presentation of the cubic data volume lattice 54 at a different angle γ, in a first plane, then the angle ψ at which an arbitrary viewing direction 66 will be positioned with respect to both the object volume 52 and data volume 54. The apparent dimensions of each voxel are going to change as the effective elevation angles ψ and γ change. If the aspect ratio A (defined as the ratio of the actual slice thickness T in object volume 52 to the actual pixel size S in the same object volume 52) is not unity (i.e., is greater or less than unity, as the object voxel is not a cubic voxel, as will be encountered in data volume 54), then the angles ψ and γ of elevation will be different, and the effective elevation angle ψ in the data volume will be different than the actual elevation angle γ in the object volume. Rotation of the data is in accordance with an object elevation angle obtained by:

$$\psi = \tan^{-1}\left(\frac{1}{A}\tan[\gamma]\right)$$

Thereafter, the projected data can be scaled to have the correct height (if rotation is about the horizontal axis) in the object volume, by multiplication of all projected data heights by the elevation scale factor. The old projected image height H can be corrected with an effective scale factor $E_s$, where $$E_s = \sqrt{(A\cos\gamma)^2 + \sin^2\gamma}$$

and the new height $H'=H\cdot E_s$. The same is true for the width when rotation is about the vertical axis.

Utilizing the above relationship, the rotation of data volume angles (α,β) becomes angles (θ,φ), because the distortion is only along one axis, so that angle θ equals angle α. The elements of the 3×3 rotational matrix [M] can be determined, and given the two involved rotational angles, these relationships are used to determine the data volume-to-image plane transformations:

X'=M1X+M2Y+M3Z+XO

Y'=M4X+M5Y+M6Z+YO where M1–M6 are the first two rows of the rotational matrix (i.e., M1=−sin θ, M2=cos θ sin ψ, M3=0, M4=−cos θ sin ψ2, M5=−sin θ sin ψ, and M6=cos ψ), X' and Y' are the locations on the image plane of the projected point, and XO and YO are image plane X and Y offsets (respectively referenced to the X and Y lowest value points) at which the selected portion of the image plane begins. After the data is projected onto image plane 56, the image is scaled to correct for the effect of the anisotropic object voxels. It will be seen that factors M1–M6 can be precalculated (step 32 in FIG. 3) at the beginning of a projection (given θ and φ) and used for all rotation calculations.

Figure 6:
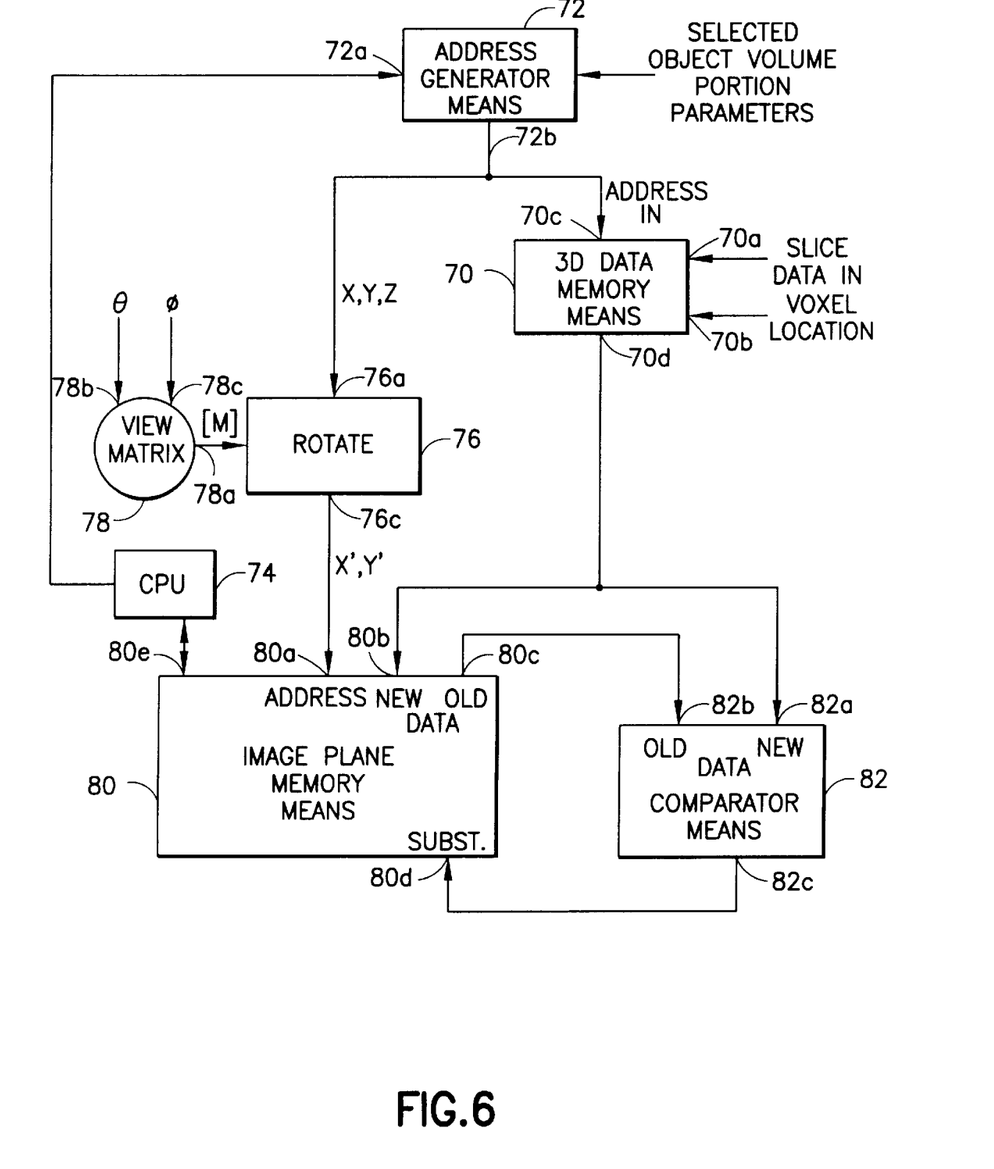
FIG. 6 is a schematic block diagram of means for providing a maximum intensity projection in three-dimensional ultrasound imaging.

FIG. 6 shows means for performing the above-described ray-casting technique which are incorporated in the master controller 8 (or a separate dedicated processor). Such means comprise a three-dimensional data memory means 70 for storing slice data as received at a data input 70a from cine memory 24. The data associated with each object voxel is stored at the address of that voxel, responsive to voxel address input information received at a voxel address input 70b from a CPU 74. Once the data memory means is filled (corresponding to the transfer of all required data from object volume 52 to data volume 54), the object volume portion of interest is selected and data establishing its starting corner and extent in the X, Y and Z directions is sent from CPU 74 to an input 72a of an address generator means 72. Means 72 sequentially provides, at an address output 72b, the X,Y,Z addresses of each voxel within the object volume selected. Output 72b is connected to an output-data-address input 70c of data memory means 70, causing the stored intensity data for that one voxel then addressed to be output from data memory means output 70d. The sequence of voxel X,Y,Z addresses is also provided to a first input 76a of a rotational parameter calculation means 76, which receives angle (α,β) information via CPU 74 as the calculated matrix element M1–M6 values, to provide at an output 76c the address X',Y' of the image plane pixel corresponding to that object X,Y,Z pixel when viewed at a selected viewing angle (θ,φ). The viewing angle (θ,φ) information is entered into the system and processed by CPU 74. The results are entered into inputs 78b and 78c of a viewing matrix means 78, to provide matrix elements M1–M6 at its output 78a and thence to rotational parameter calculation means 76. The image plane pixel address X',Y' appears at an address input 80a of a frame buffer acting as an image plane memory means 80. Simultaneously, the intensity data, projected from the data volume to the projection plane, appears at the image plane memory means new data input 80b, from three-dimensional data memory means output 70d. This data also appears at the new data input 82a of a data comparator means 82. Intensity data previously saved in the image plane memory means 80 for that address, at input 80a, appears at an old data output 80c, and thence at an old data input 82b of the comparator means. The old and new data at inputs 82b/82a, respectively, are compared in means 82 and an output 82c thereof is enabled to a selected logic condition (e.g., a high logic level) if the new data at input 82a has greater amplitude than the old data at input 82b. Output 82c is connected to a substitute-control data input 80d of the image plane memory means, to cause the data stored at the address controlled by input 80a to be changed to accept the new data at input 80b, if the substitute-data control input 80d is at the selected logic level. Thus, the stored data is initially reset, as by a signal through a data/control port 80e (from CPU 74), and the data of greatest value is stored for each image plane pixel location X',Y' responsive to a comparison indicating that the new data exceeds the value of the previously stored old data. After all of the selected addresses are sequentially scanned by address generator 72, the data stored in image plane memory means 80 is scaled in CPU 74, and the scaled image plane data can be withdrawn from memory means 80 for display, permanent storage or similar purposes.

Figure 3:
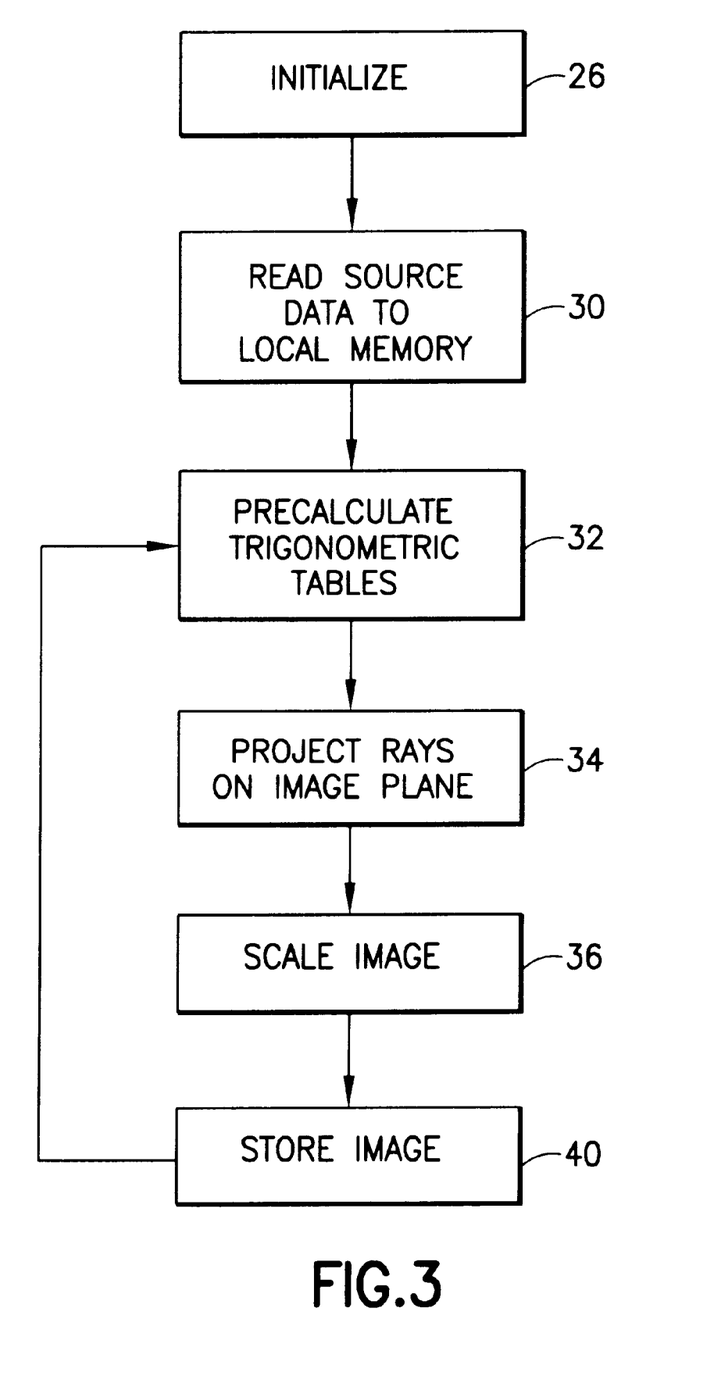
FIG. 3 is a flowchart showing the steps of an algorithm for reconstructing frames comprising successive volumetric projections of pixel intensity data in accordance with the invention.

In accordance with the invention, the method shown in FIG. 3 is applied to the color flow velocity data for the data volume of interest retrieved from the cine memory. Each pixel in the projected image includes a respective transformed velocity datum derived by projection onto a given image plane. In addition, at the time when the cine memory was frozen by the operator, the CPU 42 stored the last frame from the X-Y memory 18 at multiple successive addresses in section 24B of cine memory 24. The projected image data for the first projected view angle is written into the first address in cine memory section 24B, so that the projected image data in a region of interest is superimposed on the background frame. This process is repeated for each angular increment until all projected images are stored in cine memory section 24B, each projected image frame consisting of a region of interest containing transformed data and, optionally, a background perimeter surrounding the region of interest consisting of background frame data not overwritten by region-of-interest transformed data. The background image makes it clearer where each displayed projection is viewed from. The operator can then select any projected image for display. In addition, the sequence of projected images can be replayed on the display monitor to depict the object volume as if it were rotating in front of the viewer.

In accordance with a preferred embodiment of the invention, the ultrasound imaging system has a plurality of different projection modes. For example, the projection may include maximum or minimum value pixels. In accordance with a further mode, the ray-casting technique can be employed to provide a surface rendering.

When forming the velocity source data volume, two types of gating can used to identify the frames or scans from which velocity data will be taken. If the system operator is interested in blood flow at some point in the patient's cardiac cycle, the system is connected to receive an output from a cardiac monitor, to which the patient is connected. Every cycle the monitor outputs a signal in response to the occurrence of a predetermined characteristic in the cardiac cycle waveform. In response to every output from the monitor, the master controller stores in cine memory the frame which is present in the X-Y memory when the trigger event occurred or at a predetermined delay interval subsequent to the trigger event. Thus, one frame per cycle is stored in cine memory. Alternatively, multiple successive frames are stored in cine memory at the acoustic frame rate in response to the occurrence of a predetermined characteristic in the cardiac cycle waveform.

Regardless of which frame acquisition mode is employed, the source data volume is formed by retrieving from cine memory the pixel data corresponding to a region of interest in each frame and then processing the pixel data to acquire only pixel data having a velocity component lying within a predetermined threshold range, e.g., a non-zero velocity component. This velocity information is then projected onto various imaging planes to reconstruct projected velocity images for display.

The foregoing preferred embodiment has been disclosed for the purpose of illustration. Variations and modifications of the basic concept of the invention will be readily apparent to those skilled in the arts of ultrasound imaging or computer graphics. All such variations and modifications are intended to be encompassed by the claims set forth hereinafter.

What is claimed is:

1. A system for three-dimensional imaging of an object volume containing moving ultrasound scatterers, comprising:

an ultrasound transducer array for transmitting ultrasound beams and detecting ultrasound echoes reflected from said object volume at a multiplicity of sample volumes;

means for acquiring velocity data derived at least in part from ultrasound echoes reflected by the ultrasound scatterers, each velocity datum corresponding to a respective one of said multiplicity of sample volumes;

memory means for storing velocity data for each of said multiplicity of sample volumes;

means for retrieving a source velocity data set from the velocity data stored in said memory means, said source velocity data set including only velocity data lying in a predetermined range;

means for projecting the velocity data in said source velocity data set onto a first image plane, thereby forming a projected velocity data set representing a first projected image;

a display monitor; and means for displaying said first projected image on said display monitor.

2. The system as defined in claim 1, further comprising:

means for projecting the velocity data in said source velocity data set onto a second image plane which is rotated relative to said first image plane, thereby forming a projected velocity data set representing a second projected image; and means for displaying said second projected image on said display monitor.

3. The system as defined in claim 1, wherein at least one frame of velocity data is stored in said memory means in response to a predetermined characteristic in a cardiac cycle waveform of a patient.

4. A method for three-dimensional imaging of an object volume containing moving ultrasound scatterers, comprising the steps of:

transmitting ultrasound beams into said object volume;

detecting ultrasound echoes reflected from said object volume at a multiplicity of sample volumes;

acquiring velocity data derived at least in part from ultrasound echoes reflected by the ultrasound scatterers, each velocity datum corresponding to a respective one of said multiplicity of sample volumes;

storing velocity data for each of said multiplicity of sample volumes;

retrieving a source velocity data set from the stored velocity data, said source velocity data set including only velocity data lying in a predetermined range;

projecting the velocity data in said source velocity data set onto a first image plane, thereby forming a projected velocity data set representing a first projected image; and displaying said first projected image.

5. The method as defined in claim 4, further comprising the steps of:

projecting the velocity data in said source velocity data set onto a second image plane which is rotated relative to said first image plane, thereby forming a projected data set representing a second projected image; and displaying said second projected image.

6. The method as defined in claim 4, wherein at least one frame of velocity data is stored in response to a predetermined characteristic in a cardiac cycle waveform of a patient.

7. A method for three-dimensional imaging of an object volume containing moving ultrasound scatterers, comprising the steps of:

transmitting ultrasound beams into said object volume;

detecting ultrasound echoes reflected from said object volume at a multiplicity of sample volumes;

acquiring velocity data derived at least in part from ultrasound echoes reflected by the ultrasound scatterers, each velocity datum corresponding to a respective one of said multiplicity of sample volumes;

storing velocity data for each of said multiplicity of sample volumes;

retrieving a source velocity data set from the stored velocity data, said source velocity data set including velocity data lying in a predetermined range and excluding velocity data lying outside said predetermined range;

projecting the velocity data in said source velocity data set onto a first image plane, thereby forming a projected velocity data set representing a first projected image; and displaying said first projected image.

8. The method as defined in claim 7, further comprising the steps of:

projecting the velocity data in said source velocity data set onto a second image plane which is rotated relative to said first image plane, thereby forming a projected data set representing a second projected image; and displaying said second projected image.

9. The method as defined in claim 7, wherein at least one frame of velocity data is stored in response to a predetermined characteristic in a cardiac cycle waveform of a patient.

10. An imaging system comprising:

an ultrasound transducer array comprising a multiplicity of transducer elements;

a transmit beamformer programmed to cause said transducer array to transmit in sequence a plurality of beams which scan a plane;

a receive beamformer programmed to form respective beamsummed receive signals from respective sets of signals transduced by said transducer array following transmission of said respective beams;

a first data processor programmed to derive respective sets of velocity data from respective beamsummed receive signals;

a memory for storing said sets of velocity data; a second data processor programmed to perform the steps of:
 (a) retrieving a source velocity data set from said sets of velocity data stored in said memory, said source velocity data set including only velocity data lying in a predetermined range; and
 (b) projecting the velocity data in said source velocity data set onto an image plane, thereby forming a projected velocity data set representing a projected image; and a display device for displaying said projected image.

11. An imaging system comprising:

an ultrasound transducer array comprising a multiplicity of transducer elements;

a transmit beamformer coupled to said transducer array in a transmit mode;

a receive beamformer coupled to said transducer array in a receive mode;

a memory for storing respective sets of velocity data for respective beams transmitted by said ultrasound transducer array;

a display device for displaying a projected image; and a computer programmed to perform the steps of:
 (a) controlling said transmit beamformer in said transmit mode to cause said transducer array to transmit a plurality of beams in sequence;
 (b) controlling said receive beamformer in said receive mode to form respective beamsummed receive signals from respective sets of signals transduced by said transducer array following transmission of said respective beams;
 (c) deriving respective sets of velocity data from respective beamsummed receive signals;
 (d) retrieving a source velocity data set from said sets of velocity data stored in said memory, said source velocity data set including only velocity data lying in a predetermined range; and
 (e) projecting the velocity data in said source velocity data set onto an image plane, thereby forming a projected velocity data set representing said projected image.

* * * * *